US007847119B2

(12) United States Patent
Ojima

(10) Patent No.: US 7,847,119 B2
(45) Date of Patent: *Dec. 7, 2010

(54) DRUG CONJUGATES

(75) Inventor: Iwao Ojima, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 42 days.

This patent is subject to a terminal disclaimer.

(21) Appl. No.: 11/856,317

(22) Filed: Sep. 17, 2007

(65) Prior Publication Data

US 2008/0139815 A1    Jun. 12, 2008

Related U.S. Application Data

(63) Continuation of application No. 11/053,655, filed on Feb. 8, 2005, now Pat. No. 7,282,590.

(60) Provisional application No. 60/544,033, filed on Feb. 12, 2004.

(51) Int. Cl.
*C07C 321/20* (2006.01)
(52) U.S. Cl. .................................................. 562/426
(58) Field of Classification Search .................. 562/426
See application file for complete search history.

(56) References Cited

U.S. PATENT DOCUMENTS

| | | | |
|---|---|---|---|
| 3,324,140 A | 6/1967 | Schorre et al. | |
| 3,458,563 A | 7/1969 | Cragoe, Jr. | |
| 3,600,437 A | 8/1971 | Marshall | |
| 4,049,665 A | 9/1977 | Douglass | |
| 4,258,193 A | 3/1981 | Fujii et al. | |
| 4,324,793 A | 4/1982 | Hagen et al. | |
| 4,396,621 A * | 8/1983 | Bernasconi et al. | .... 514/255.05 |
| 4,493,802 A | 1/1985 | Jaedicke et al. | |
| 4,505,917 A | 3/1985 | Menon et al. | |
| 4,880,935 A | 11/1989 | Thorpe | |
| 4,902,826 A | 2/1990 | Bauer et al. | |
| 5,002,967 A | 3/1991 | Mueller et al. | |
| 5,124,441 A | 6/1992 | Carlsson et al. | |
| 5,137,877 A | 8/1992 | Kaneko et al. | |
| 5,274,184 A | 12/1993 | Nagl et al. | |
| 5,932,731 A | 8/1999 | Goda et al. | |
| 5,936,092 A | 8/1999 | Shen et al. | |
| 6,008,321 A | 12/1999 | Li et al. | |
| 6,313,150 B1 | 11/2001 | Ohtsuka et al. | |
| 7,282,590 B2 * | 10/2007 | Ojima | ......................... 548/259 |
| 2003/0100607 A1 | 5/2003 | Tsukamoto et al. | |

FOREIGN PATENT DOCUMENTS

JP             5363336         6/1978

OTHER PUBLICATIONS

Srogl et al. CAS Acession No. 1999:629460.*
Ojima et al., "Tumor-Specific Novel Taxoid—Monoclonal Antibody Conjugates," J. Med. Chem. 2002, 45:5620-5623.
Y. Ueda, "Novel Water Soluble Phosphate Prodrugs of Taxol® Possessing in Vivo Antitumor Activity", *Bioorganic & Medicinal Chemistry Letters*, vol. 3, No. 8, pp. 1761-1766 (1993).
I. Ojima et al., "Syntheses and Structure—Activity Relationships of the Second-Generation Antitumor Taxoids: Exceptional Activity against Drug-Resistant Cancer Cells", *J. Med. Chem.*, vol. 39, No. 20, pp. 3889-3896 (1996).
M.P. Dillon et al. "Application of the 'Trimethyl Lock' to Ganciclovir, a Pro-Prodrug with Increased Oral Bioavailability", *Bioorganic & Medicinal Chemistry Letters*, vol. 6, No. 14, pp. 1653-1656 (1996).
B. Wang et al., "Synthesis of a Novel Esterase-Sensitive Cyclic Prodrug System for Peptides that Utilizes a 'Trimethyl Lock'-Facilitated Lactonization Reaction", *J. Org. Chem.*, vol. 62, No. 5, pp. 1363-1367 (1997).
I. Ojima et al., "Synthesis and Structure—Activity Relationships of New Second-Generation Taxoids", *Bioorg. Med. Chem. Lett.*, vol. 9, pp. 3423-3428 (1999).
R.B. Greenwald et al., "Drug Delivery Systems Based on Trimethyl Lock Lactonization: Poly(ethylene glycol) Prodrugs of Amino-Containing Compounds", *J. Med. Chem.*, vol. 43, No. 3, pp. 475-487 (2000).
K. Achilles, "Coumarin Derivatives as Protease-Sensitive Prodrugs", *Arch. Pharm. Pharm. Med. Chem.*, vol. 334, pp. 209-215 (2001).
M.R. Vredenburg et al., "Effects of Orally Active Taxanes on P-Glycoprotein Modulation and Colon and Breast Carcinoma Drug Resistance", *Journal of the National Cancer Institute*, vol. 93, No. 16, pp. 1234-1245 (2001).
Block et al., Antithrombotic Organosulfur Compounds from Garlic: Structural, Mechanistic, and Synthetic Studies, J. Am. Chem. Soc., vol. 108, pp. 7045-7055 (1986).
Bressler et al., "Identification of disulfides from the biodegradation of dibenzothiophene," Applied and Environmental Microbiology, vol. 17(11), pp. 5084-5093 (2001).

* cited by examiner

*Primary Examiner*—Joseph R Kosack
(74) *Attorney, Agent, or Firm*—Hoffman & Baron, LLP

(57) ABSTRACT

A compound having the formula Y-A-Z, wherein:
  A is a phenyl group which is unsubstituted or substituted;
  Y and Z are substituents at adjacent positions on ring A;
  Y represents:

$$-C_a(R^1)(R^2)-C_b(R^3)(R^4)-\overset{O}{\underset{\|}{C}}-X-G;$$

Z represents:

$$-S-S-J;$$

and wherein the remaining variables are as defined in the specification.

23 Claims, No Drawings

DRUG CONJUGATES

CROSS-REFERENCE TO RELATED APPLICATION

This application is a continuation of U.S. application Ser. No. 11/053,655, filed on Feb. 8, 2005 (now U.S. Pat. No. 7,282,590), which asserts priority to U.S. Provisional Application Ser. No. 60/544,033, filed on Feb. 12, 2004. Both of the aforementioned applications are hereby incorporated by reference in their entireties.

The present invention was made with government support under Grant No. R01 GM427980 as well as R01CA103314 awarded by the National Institutes of Health. The United States government has certain rights in this invention.

BACKGROUND OF THE INVENTION

The advantage of drugs that are capable of selectively targeting a specific cell type is well recognized. Thus, designing such selective drugs is a field of intense study. Such drugs are often, but by no means always, anticancer drugs.

Of importance in this regard, are drugs (or pro-drugs) that are bound to a marker. The purpose of the marker is to direct the drug to a marker-specific target cell. For example, binding drugs to antibodies for the purpose of targeting antibody-specific cells, such as tumor cells, is well known.

Binding a marker directly to a drug is, however, not always feasible. In addition, binding a marker directly to a drug often has the effect of dramatically reducing the efficacy of the drug, or disabling the action of the drug completely.

One approach to reducing the loss of efficacy of a drug bound to a marker is to bind the marker to the drug in a way that causes the drug to be released at the target in its most active form (usually the parent drug itself. In this regard, there has been intense interest in finding heterobifunctional compounds, or linkers, that not only bind a marker and a drug, but that also cause the drug to be released in its most active form at the appropriate time.

For example, U.S. Pat. No. 4,880,935 to Thorpe and U.S. Pat. No. 5,936,092 to Shen, et al. disclose heterobifunctional compounds that contain a disulfide group at one end and a carboxylate group at the other end. A cytotoxin is bound to the disulfide group at one end. An antibody is bound to the carboxylate group at the other end. Once in the targeted cell, the disulfide bond is cleaved by endogenous disulfide-reducing peptides, such as glutathione (GT). Cleavage of the disulfide bond releases the parent cytotoxin inside the targeted cell.

Similarly, U.S. Pat. No. 5,137,877 to Kaneko, et al., disclose heterobifunctional compounds that contain a hydrazinyl group at one end and a disulfide group at the other end. An anthracycline-based cytotoxin is bound to the hydrazinyl group. An antibody is bound to the disulfide group. The more acidic environment of the target cells causes hydrolysis of the hydrazinyl group. Hydrolysis of the hydrazinyl group releases the parent cytotoxin.

However, a demonstrated release of the drug at a target does not necessarily make the heterobifunctional compound medically effective or desirable. Medical efficacy depends to a significant extent on the rate of release of the drug by the heterobifunctional compound.

Accordingly, there have been efforts to increase the rates of release of drugs at a specified target by designing new heterobifunctional compounds. Most notable are efforts to design heterobifunctional compounds that, when hydrolyzed, undergo a favorable cyclization reaction to release the drug.

For example, Y. Ueda et al., *Bioorganic & Medicinal Chemistry Letters,* 1993, Vol. 3, No. 8, 1761-1766, disclose linkers that undergo phosphatase-initiated lactonization of phosphonoxyphenylpropionate derivatives of Taxol. The lactonization results in the in vivo release of the parent Taxol. As shown in Ueda et al., the purpose of Ueda's phosphonoxyphenylpropionate group is to increase the water solubility of Taxol.

R. B. Greenwald et al., *J. Med. Chem.,* 2000, 43, 475-487, disclose ester-containing compounds linked to a drug to form a pro-drug. The pro-drug is hydrolyzed by an esterase, which results in a lactonization reaction. The lactonization reaction releases the drug.

K. Achilles, *Arch. Pharm. Pharm. Med. Chem.,* 2001, 334, 209-215, discloses esterase-initiated lactonization of heterobifunctional compounds containing a peptide binding agent and a pro-drug. The lactonization causes release of the drug. The peptides bind to polymorphonuclear elastase, a serine protease associated with numerous medical conditions, including cancer.

Similarly, B. Wang et al. J. Org. Chem., 1997, 62, 1363-1367, disclose esterase-initiated lactonization of prodrugs containing cyclic peptides as binding agents.

However, the efficacy of conjugates of the heterobifunctional compounds described above is, in the vast majority of cases, far from clinically useful. For example, it would be particularly beneficial to increase the rates of drug release of such conjugates in order to be clinically effective.

Such targeted and effective rates of release of drugs have not yet been realized. In the case of targeting tumor cells, such high rates of release of anti-cancer drugs are particularly critical in light of the known high proliferation of cancer cells in tumors.

In addition, the drug conjugate containing a linker should release the most active form of the drug. See I. Ojima, X. Geng, X. Wu, C. Qu, C. P. Borella, H. Xie, S. D. Wilhelm, B. A. Leece, L. M. Bartle, V. S. Goldmacher, and R. V. J. Chari, J. Med. Chem. 45, 5620-5623 (2002).

Taxol, a diterpene natural product, has gained prominence as one of the most efficacious anticancer drugs. See E. K. Rowinsky, Annual Review of Medicine 1997, 48, 353; M. Suffness, Taxol Science and Applications; CRC Press: New York, 1995. Even more promising congeners of Taxol, termed taxoids (Taxol-like compounds), with orders of magnitude higher potency than Taxol have been developed. See G. I. Georg, T. Chen, I. Ojima, and D. M. Vyas (Eds.), "Taxane Anticancer Agents: Basic Science and Current Status", ACS Symp. Series 583; American Chemical Society, Washington, D. C., 1995); I. Ojima, et al, Bioorg. Med. Chem. Lett., 1999, 9, 3423-3428; I. Ojima, et al, J. Med. Chem., 1996, 39, 3889-3896; and I. Ojima, G. D. Vite, K.-H. Altmann (Eds.), "Anticancer Agents: Frontiers in Cancer Chemotherapy", ACS Symp. Series 796, American Chemical Society, Washington, D. C., 2001.

However, Taxol, taxoids, and other cytotoxic anticancer drugs contain drawbacks, including high toxicity to normal cells, poor water solubility, and emergence of drug-resistance. Therefore, there has been particular interest in selectively and efficiently targeting tumor cells with cytotoxic anticancer drugs. See, for example, K. Achilles, Arch. Pharm. Pharm. Med. Chem., 2001, 334, 209-215, and U.S. Pat. No. 5,137,877 to Kaneko, et al. R. V. J. Chari, Advanced Drug Delivery Reviews, 1998, 31, 89-104; M. L. Disis and M. A. Cheever, Advances in Cancer Research, 1997, 71, 343-371; H. Bier, T. Hoffmann, I. Haas, A. Van Lierop, Cancer Immunology Immunotherapy, 1998, 46, 167-173; G. A. Pietersz, B. Toohey, I. F. C. McKenzie, Journal of Drug Targeting, 1998, 5, 109-120; P. R. Hamann, L. M. Hinman, I. Hollander, C. F. Beyer, D. Lindh, R. Holcomb, W. Hallett, H.-R. Tsou, J. Upeslacis, D. Shochat, A. Mountain, D. A. Flowers, I. Bernstein, Bioconjugate Chemistry, 2002, 13, 47-58; Firestone, R. A.; Dubowchik, G. M. In Eur. Pat. Appl. EP 0624377 (Bristol-Myers Squibb Co. USA) 1994; A. Safavy, K. P. Raisch, M. B. Khazaeli, D. J. Buchsbaum, J. A. Bonner, Journal of Medicinal Chemistry, 1999, 42, 4919-4924; C. Li, D. Yu, T. Inoue, D. J. Yang, L. Milas, N. R. Hunter, E. E. Kim, S. Wallace, Anti-Cancer Drugs, 1996, 7, 642-648; Pendri, A.; Conover, C. D.; Greenwald, R. B. Anti-Cancer Drug Design, 1998, 13, 387; C. Li, D.-F. Yu, R. A. Newman, F. Cabral, L. C. Stephens, N. Hunter, L. Milas, S. Wallace, Cancer Research, 1998, 58, 2404-2409; W. C. Rose, J. L. Clark, F. Y. F. Lee, A. M. Casazza, Cancer Chemotherapy and Pharmacology, 1997, 39, 486-492; J. J. Correa, M. Page, Tumor Targeting in Cancer Therapy, 2002, 165-178; V. Guillemard, H. U. Saragovi, Cancer Research, 2001, 61, 694-699; I. Ojima, X. Geng, X. Wu, C. Qu, C. P. Borella, H. Xie, S. D. Wilhelm, B. A. Leece, L. M. Bartle, V. S. Goldmacher, and R. V. J. Chari, J. Med. Chem. 45, 5620-5623 (2002).

Thus, there is a need for improving, inter alia, the specificity of drug delivery and the rates of release of various of drugs, including anticancer drugs. To achieve the above, there is a need for improved heterobifunctional linkers that bind a drug to a cell-specific marker, and that release the most active form of the drug in the target cell. There is a particular need for heterobifunctional linkers that selectively target tumor cells with highly potent cytotoxic drugs at a drug release rate that is effective for the destruction and/or inhibition of tumor cells.

SUMMARY OF THE INVENTION

These, and other objectives as will be apparent to those of ordinary skill in the art, have been achieved by providing a compound having the formula Y-A-Z, wherein:

A is a 5, 6, or 7 member ring that is monocyclic or is fused to 1 to 3 additional 4 to 8 member rings; wherein ring A and, independently, the fused additional rings are carbocyclic or heterocyclic, and saturated or unsaturated, wherein unsaturated rings are aromatic or non-aromatic;

ring A and the additional rings are unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, carboxyl (hydroxycarbonyl), lower alkanoyl, lower alkanoyloxy, amino, N-lower alkyl)amino, N,N-di(lower alkyl) amino, formamido (formylamino), N-acylamino, N,N-diacylamino (imido), hydrazido, N-(lower alkyl)hydrazido, N,N-di(lower alkyl)hydrazido, N-arylhydrazido, N,N-diarylhydrazido, N-(heteroaryl) hydrozido, N,N-di(heteroaryl)hydrazido, carboxamido (carbamoyl), N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl (sulfonic acid), (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl;

Y and Z are substituents at adjacent positions on ring A;

Y represents:

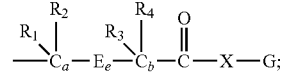

Z represents:

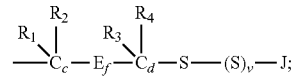

X represents O, S, or $NR^a$;
E represents O, S, or $NR^b$;
$R^a$ and $R^b$ independently represent H, lower alkyl, cycloalkyl, heterocycloalkyl, cycloalkenyl, heterocycloalkenyl, aryl, aryl lower alkyl, heteroaryl, lower alkanoyl, aromatic acyl (arenecarbonyl), heteroaromatic acyl (heteroarenecarbonyl), (lower alkoxy)carbonyl, aryloxycarbonyl, heteroaryloxycarbonyl, N-arylcarbamoyl, N,N-diarylcarbamoyl, N-heteroarylcarbamoyl, N,N-di(heteroaryl)carbamoyl, (lower alkane)sulfonyl, arenesulfonyl, or heteroarenesulfonyl, wherein the lower alkyl, lower alkanoyl and lower alkoxy groups are unsubstituted or substituted with 1 to 4 groups independently selected from aryl, heteroaryl or fluoro;
each of a, b, c, d, e and f independently represents 0 or 1;
a+c equals 0, 1, or 2;
b+d equals 0, 1, or 2;
a+b+c+d+e+f equals 1, 2, or 3;
provided that when f is 1, then d is 1, and when d is 0, then f is 0; and when both e and b are 0, then neither $R^1$ nor $R^2$ is chloro or bromo.
v represents 0 or 1, provided that when v is 0, then J is hydrogen, a metal ion, or a quaternary ammonium ion; and X is O and G is H;
each of $R^1$ and $R^2$ independently represents H, lower alkyl, aryl, heteroaryl, fluoro, chloro, bromo, lower alkoxy (i.e., alkyloxy), aryloxy, heteroaryloxy, N,N-di(lower alkyl)amino, N,N-diarylamino, N,N-di(heteroaryl) amino, (lower alkyl)thio, arylthio, heteroarylthio, (lower alkane)sulfinyl, arenesulfinyl, heteroarenesulfinyl, (lower alkyl)sulfonyl, arenesulfonyl, heteroarenesulfonyl, (lower alkoxy)-(lower alkyl), aryloxy-(lower alkyl), heteroaryloxy-(lower alkyl), N,N-di(lower alkyl) amino-(lower alkyl), N,N-diarylamino-(lower alkyl), N,N-di(heteroaryl)amino-(lower alkyl), (lower alkyl) thio-(lower alkyl), arylthio-(lower alkyl), heteroarylthio-(lower alkyl), (lower alkane)sulfinyl-(lower alkyl), arenesulfinyl-(lower alkyl), heteroarenesulfinyl-(lower alkyl), (lower alkyl)sulfonyl-(lower alkyl), arenesulfonyl-(lower alkyl), heteroarenesulfonyl-(lower alkyl), (lower alkoxy)carbonyl, aryloxycarbonyl, heteroaryloxycarbonyl, carboxamido (carbamoyl), N-(lower alkyl)carbamoyl, N,N-(lower alkyl)carbamoyl, N-arylcarbamoyl, N,N-diarylcarbamoyl, N-heteroarylcarbamoyl or N,N-di(heteroaryl)carbamoyl;
each of $R^3$ and $R^4$ independently represents H, lower alkyl, aryl, heteroaryl, fluoro, lower alkoxy, aryloxy, heteroaryloxy, N,N-di(lower alkyl)amino, N,N-diarylamino, N,N-di(heteroaryl)amino, (lower alkyl)thio, arylthio, heteroarylthio, (lower alkane)sulfinyl, arenesulfinyl, heteroarenesulfinyl, (lower alkyl)sulfonyl, arenesulfonyl, heteroarenesulfonyl, (lower alkoxy)-(lower alkyl), aryloxy-(lower alkyl), heteroaryloxy-(lower alkyl), N,N-di(lower alkyl)amino-(lower alkyl), N,N-diarylamino-(lower alkyl), N,N-di(heteroaryl)amino-(lower alkyl), (lower alkyl)thio-(lower alkyl), arylthio-(lower alkyl), heteroarylthio-(lower alkyl), (lower alkane)sulfinyl-(lower alkyl), arenesulfinyl-(lower alkyl), heteroarenesulfinyl-(lower alkyl), (lower alkyl) sulfonyl-(lower alkyl), arenesulfonyl-(lower alkyl), heteroarenesulfonyl-(lower alkyl), (lower alkoxy)carbonyl, aryloxycarbonyl, heteroaryloxycarbonyl, carboxamido (carbamoyl), N-(lower alkyl)carbamoyl or N,N-(lower alkyl)carbamoyl, N-arylcarbamoyl, N,N-diarylcarbamoyl, N-heteroarylcarbamoyl or N,N-di(heteroaryl)carbamoyl;

$R^1$ and $R^2$ or $R^3$ and $R^4$ are optionally connected to form a 3 to 8 member ring, wherein the 3 to 8 member ring is cycloalkyl, heterocycloalkyl, cycloalkenyl, heterocycloalkenyl, aryl, or heteroaryl;

lower means having 1-6 carbon atoms;

either G is hydrogen, a metal ion, a quaternary ammonium ion, lower alkyl, or comprised of a pharmaceutically active chemical compound or the precursor thereof; or X-G represents a carbonyl-activating group;

J is lower alkyl, aryl, heteroaryl, omega-hydroxycarbonyl-(lower alkyl), omega-(lower alkoxy)carbonyl-(lower alkyl), omega-(X-G)-carbonyl-(lower alkyl) group, or comprised of a specific binding agent.

DETAILED DESCRIPTION OF THE INVENTION

The invention relates to a drug conjugate having the formula Y-A-Z. In the formula, A is a 5, 6, or 7 member ring. In one embodiment, ring A is monocyclic and carbocyclic. The monocyclic, carbocyclic ring may be saturated. Some examples of suitable saturated rings include cyclopentane, cyclohexane, and cycloheptane rings.

Alternatively, the monocyclic carbocyclic ring may be unsaturated. The unsaturated ring contains at least one double bond. For example, a 5 member ring can have 1 or 2 double bonds, and a 7 member ring can have 1 to 3 double bonds. The unsaturated rings may be aromatic, i.e., "aryl" or "arene," or non-aromatic. Some examples of suitable unsaturated monocyclic carbocyclic rings include cyclopentene, cyclohexene, cycloheptene, cyclopentadiene, 1,3-cyclohexadiene, 1,4-cyclohexadiene, 1,3-cycloheptadiene, and cycloheptatriene rings. Preferably, the unsaturated carbocyclic ring is a benzene ring, i.e., phenylene.

In another embodiment, ring A is a heterocyclic ring. The heterocyclic ring contains at least one, and up to four, of any of the heteroatoms nitrogen (N), oxygen (O), or sulfur (S), or any combination thereof. The nitrogen and sulfur heteroatoms may also contain additional substituents. For example, a nitrogen heteroatom may be an amine oxide, oxime, O-(lower alkyl)-oxime, hydroxylamine, O-(lower alkyl)-hydroxylamine, hydrazine, N-(lower alkyl)-hydrazine, N,N-di(lower alkyl)-hydrazine, N-arylhydrazine, N,N-diarylhydrazine, or hydrazone; and a sulfur heteroatom may be a sulfoxide or sulfone. In addition, where the nitrogen is not double bonded within the ring, the nitrogen may be substituted by H, lower alkyl, cycloalkyl, heterocycloalkyl, cycloalkenyl, heterocycloalkenyl, aryl, heteroaryl, lower alkanoyl, arenecarbonyl, heteroarenecarbonyl, (lower alkoxy)carbonyl, aryloxycarbonyl, heteroaryloxycarbonyl, carboxamido (carbamoyl), N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, (lower alkane)sulfinyl, arenesulfinyl, heteroarenesulfinyl, (lower alkane)sulfonyl, arenesulfonyl, or heteroarenesulfonyl.

In one embodiment, the heterocyclic ring may be saturated. Some examples of suitable saturated heterocyclic rings containing a single nitrogen heteroatom include pyrrolidine, piperidine, homopiperidine (azepane), N-methylpyrrolidine, N-(tert-butoxycarbonyl)pyrrolidine, N-acetylpyrrolidine, pyrrolidine N-oxide, pyrrolidine N-hydroxide, pyrrolidine N-methoxide, N-methylpiperidine, N-acetyl piperidine, piperidine N-oxide, piperidine N-hydroxide, piperidine N-methoxide, and N-benzylpiperidine rings.

Some examples of suitable saturated heterocyclic rings containing more than one nitrogen heteroatom include imidazolidine, N,N'-dimethylimidazolidine, pyrazolidine, piperazine, 1-acetylpiperazine, 1-(o-tolyl)piperazine, piperazine-N,N'-dioxide, tert-butyl-4-benzyl-1-piperazinecarboxylate, 1-benzylpiperazine, benzyl 1-piperazinecarboxylate, hexahydropyrimidine, homopiperazine (1,4-diazepane), tert-butyl 1-homopiperazinecarboxylate, benzyl 1-homopiperazinecarboxylate, hexahydro-1,3,5-triazine (1,3,5-triazinane), 1,3,5-trimethylhexahydro-1,3,5-triazine, 1,3,5-triacryloylhexahydro-1,3,5-triazine, and 1,3,5-tribenzylhexahydro-1,3,5-triazine rings.

Some examples of suitable saturated heterocyclic rings containing a single oxygen heteroatom include tetrahydrofuran, tetrahydropyran, and oxacycloheptane (oxepane) rings. Some examples of suitable saturated 5, 6, or 7 member heterocyclic rings containing more than one oxygen heteroatom include 1,3-dioxolane, 1,3-dioxane, 1,4-dioxane, and 1,3-dioxepane rings.

Some examples of suitable saturated heterocyclic rings containing a single sulfur heteroatom include tetrahydrothiophene, tetrahydrothiopyran, thiacycloheptane (thiepane), tetrahydrothiophene 1-oxide, tetrahydrothiophene-1,1-dioxide (tetramethylene sulfone, or sulfolane), and tetrahydrothiopyran-1,1-dioxide rings. Some examples of suitable saturated 5, 6, or 7 member heterocyclic rings containing more than one sulfur heteroatom include 1,3-dithiolane, 1,3-dithiane, 1,4-dithiane, 1,3-dithiepane, 1,1,3,3-tetramethyl-1,3-dithiolane, and 1,1,4,4-tetramethyl-1,4-dithiane rings.

Some examples of suitable saturated heterocyclic rings containing a combination of 2 to 4 heteroatoms include 1,3-oxazolidine, N-butyl-oxazolidine, 1,3-thiazolidine, 1,3-oxathiolane, morpholine, thiomorpholine (1,4-thiazinane), 4-acetylmorpholine, 1,4-oxathiane, 1,3-oxazinane, 1,3-thiazinane, 4-aza-1-oxa-cycloheptane (1,4-oxazepane), 1,3,4-oxadiazolidine, 1,3,5-oxadiazinane, 1,3,2-dioxathiolane 2,2-dioxide, and 1-oxahexahydro-3,4,5-triazine (1-oxa-3,4,5-triazinane) rings.

Alternatively, the heterocyclic ring may be unsaturated. The unsaturated heterocyclic rings may be aromatic, i.e., "heteroaryl" or "heteroarene," or non-aromatic. Some examples of suitable unsaturated heterocyclic rings containing a single nitrogen heteroatom include 1H-pyrrole, 2,5-dihydro-1H-pyrrole, pyridine, pyridine N-oxide, 1-aza-2,4,6-cycloheptatriene (azepine), tert-butyl 2,5-dihydro-1H-pyrrole-1-carboxylate, 1-(p-toluenesulfonyl)pyrrole, and 4-(benzyloxy)pyridine N-oxide rings. Some examples of suitable unsaturated heterocyclic rings containing more than one nitrogen heteroatom include imidazole, 1H-pyrazole, pyrazine, pyrimidine, 1,3,5-triazine, 1H-1,2,3-triazole, 1H-1, 2,4-triazole, 1-(p-toluenesulfonyl)imidazole, 1-acetylimidazole, 1-(tert-butoxycarbonyl)imidazole, and 1,1'-sulfonyldiimidazole rings.

Some examples of suitable unsaturated heterocyclic rings containing a single oxygen heteroatom include furan, 2,5-dihydrofuran, 2,3-dihydrofuran, 2H-pyran, 4H-pyran, 3,4-dihydro-2H-pyran, and 1-oxa-2,4,6-cycloheptatriene (oxepine) rings. Some examples of suitable unsaturated heterocyclic rings containing more than one oxygen heteroatom include 1,3-dioxacyclopent-4-ene (1,3-dioxole), 1,3-dioxacyclohex-4-ene (4H-1,3-dioxine), 1,4-dioxacyclohex-2-ene (2,3-dihydro-1,4-dioxine), and 1,4-dioxacyclohexa-2,5-diene (1,4-dioxine) rings.

Some examples of suitable unsaturated heterocyclic rings containing a single sulfur heteroatom include thiophene, thiophene-1,1-dioxide, 2,5-dihydrothiophene, 2,5-dihydrothiophene-1-oxide (butadiene sulfoxide), 2,5-dihydrothiophene-1,1-dioxide (butadiene sulfone), 2,3-dihydrothiophene, 2H-thiopyran, 4H-thiopyran, 3,4-dihydro-2H-thiopyran, 4H-thiopyran-1,1-dioxide, and 1-thia-2,4,6-cycloheptatriene (thiepine) rings. Some examples of suitable unsaturated 5, 6, or 7 member heterocyclic rings containing more than one sulfur heteroatom include 1,3-dithiacyclopent-4-ene (1,3-dithiole), 1,3-dithiacyclohex-4-ene (4H-1,3-dithiine), 1,4-dithiacyclohex-2-ene (2,3-dihydro-1,4-dithiine), 1,3-dithiacyclohept-5-ene (4,7-dihydro-1,3-dithiepine), and 1,4-dithiacyclohexa-2,5-diene (1,4-dithiine) rings.

Some examples of suitable unsaturated heterocyclic rings containing a combination of 2 to 4 heteroatoms, include oxazole, thiazole, oxathiole, 2H-1,4-oxazine, 4H-1,4-oxazine, 2H-1,3-oxazine, 1,4-oxazine-4-carboxylic acid tert-butyl ester, 1,4-oxazine-4-carboxylic acid phenathren-1-ylmethyl ester, 2H-1,4-thiazine, 4H-1,4-thiazine, 2H-1,3-thiazine, 1-thia-4-oxacyclohexa-2,5-diene (1,4-oxathiine), 1,3,4-oxadiazole, 4H-1,3,5-oxadiazine, 4H-1,3,4,5-oxatriazine, and 1-oxa-4-aza-cyclohept-2-ene (4,5,6,7-tetrahydro-1,4-oxazepine) rings.

Any of the monocyclic rings, A, described above, may be fused to 1 to 3 additional 4 to 8 member rings, as long as ring A has two adjacent positions The additional rings are fused either directly to ring A or to each other.

The additional 4 to 8 member fused rings include all of the rings previously described for ring A. However, the additional rings also include 4 and 8 member rings not included for ring A. For example, some carbocyclic 4 and 8 member rings include cyclobutane, cyclooctane, cyclobutene, cyclooctene, 1,3-cyclooctadiene, 1,5-cyclooctadiene, and 1,3,5,7-cyclooctatetraene rings.

Some examples of additional saturated heterocyclic 4 and 8 member rings include azetidine (1-azacyclobutane or trimethylene imine), oxetane (1-oxacyclobutane or trimethylene oxide), thietane (1-thiacyclobutane or trimethylene sulfide), azocane (1-azacyclooctane or heptamethylene imine), oxocane (1-oxacyclooctane or heptamethylene oxide), and thiocane (1-thiacyclooctane or heptamethylene sulfide) rings. Some examples of additional unsaturated heterocyclic 4 and 8 member rings include 1-thiacyclobut-2-ene (2H-thiete), 1-oxacyclobut-2-ene (2H-oxete), 1-azacyclobut-2-ene (1,2-dihydroazete), 1-thiacycloocta-2,4,6-triene (2H-thiocine), 1-oxacycloocta-2,4,6-triene (2H-oxocine), and 1-azacyclocta-2,4,6-triene (2H-azocine) rings.

The fused rings may be all carbocyclic, and independently, saturated or unsaturated. Some examples of a carbocyclic ring fused to one 4 to 8 member carbocyclic ring, wherein all of the carbocyclic rings are saturated, include bicyclo[3.3.0]octane (octahydropentalene), bicyclo[4.3.0]nonane (octahydroindene), bicyclo[4.4.0]decane (decahydronaphthalene), bicyclo[6.3.0]undecane (decahydrocyclopentacyclooctene or decahydrocyclopenta[8]annulene), and bicyclo[4.2.0]octane rings.

Some examples of carbocyclic rings fused to two or three 4 to 8 member carbocyclic rings, wherein the carbocyclic rings are all saturated, include tetradecahydroanthracene, tetradecahydrophenanthrene, octadecahydrotriphenylene, dodecahydrobiphenylene, hexadecahydrodibenzo[a,e]cyclooctene, eicosahydrotribenzo[a,c,e]cyclooctene, octadecahydro-2,3-benzanthracene (octadecahydronaphthacene), hexadecahydrocyclopenta[a]phenanthrene, octadecahydro-1,2-benzanthracene (octadecahydro-benzo[a]anthracene), hexadecahydropyrene, and octadecahydrochrysene rings.

Alternatively, the fused carbocyclic rings may be composed of one or two rings that are saturated and one or two rings that are unsaturated. Some examples of a carbocyclic ring fused to 1 to 3 additional carbocyclic 4 to 8 member rings, wherein at least one of the rings is saturated and at least one of the other rings is unsaturated include bicyclo[4.3.0]non-3-ene, bicyclo[4.3.0]non-7-ene, bicyclo[4.4.0]dec-8-ene, and bicyclo[4.4.0]dec-7,9-diene rings.

Alternatively, all of the fused carbocyclic rings mail be unsaturated. Some of the unsaturated carbocyclic rings may also be aromatic. Some examples of a carbocyclic ring fused to 1 to 3 additional 4 to 8 member carbocyclic rings, wherein all of the carbocyclic rings are unsaturated, include naphthalene, phenanthrene, anthracene, triphenylene, azulene, chrysene, pyrene, biphenylene, bicyclo[4.3.0]non-3-ene, bicyclo[4.3.0]non-7-ene, bicyclo[4.4.0]dec-8-ene, bicyclo[4.4.0]dec-1-ene, bicyclo[4.4.0]dec-7,9-diene, bicyclo[4.3.0]nona-2,4,7-triene, bicyclo[4.4.0]deca-2,4,7,9-tetraene, bicyclo[4.4.0]deca-1,3,8-triene, 1,4,5,8-tetrahydronaphthalene, cyclopentacyclooctene (cyclopenta[8]annulene), dibenzo[a,e]cyclooctene, tribenzo[a,c,e]cyclooctene, 2,3-benzanthracene, 1,2-benzanthracene, and cyclopenta[a]phenanthrene rings.

In another embodiment, the carbocyclic ring may be fused to 1 to 3 additional heterocyclic 4 to 8 member rings. Some examples of such compounds include indoline, 1-acetylindoline, 2,3-benzofuran, thianapthene, quinoline, isoquinoline, phthalazine, decahydroquinoline, cyclopentyl[b]pyridine (6,7-dihydro-5H-[1]pyrindine), benzimidazole, benzothiazole, benzisoxazole, benzodioxole, quinoxaline, quinazoline, benzoxazine, cinnoline, 2-cyclopenten-1-one ethylene ketal, 1,4-cyclohexanedione bis(ethylene ketal), benzofurazan, 1,10-phenanthroline, 4,7-phenanthroline, 1,7-phenanthroline, 2,1,3-benzothiadiazole, benzofuroxan, benzotriazole, 1-acetylbenzotriazole, 6,7-dihydro-5H-cyclohepta[2,1-b;3,4-b']dipyridine, benzo[b]oxepine, benzo[b]azepine, benzo[b]oxocine, benzo[b]azocine, and 7-oxa-bicyclo[4.2.0]octa-1,3,5-triene rings.

In a further embodiment, the carbocyclic ring may be fused to 2 or 3 additional 4 to 8 member rings, which are a mixture of carbocyclic and heterocyclic rings. Some examples of such compounds include acridine, phenazine, 5,10-dihydro-5,10-dimethylphenazine, phenanthridine, 9H-carbazole, dibenzofuran, xanthene, dibenzothiophene, phenoxazine, phenothiazine, phenoxathiin, dibenzo[b]azepine, 5H-dibenzo[b]azepine-5-carboxamide, 6,11-dihydrodibenzo[b,e]oxepine, and benz[a]phenoxazine, and 6,11-dihydrodibenzo[b,e]thiepine rings.

In a different embodiment, ring A is a heterocyclic ring fused to 1 to 3 additional 4 to 8 member rings that are also heterocyclic. Some examples of such compounds include 1,3,5,8-tetraazanaphthalene (pteridine), 1,2,4-triazolo[1,5-a]pyrimidine, 1H-1,2,3-triazolo[4,5]pyridine, 1-acetyl-1H-1,2,3-triazolo[4,5-b]pyridine, 7H-purine, 1,2,4-triazolo[4,3-a]-1,3,5-triazine (s-triazolo[4,3-a]-s-triazine), 1,3,8-triazanaphthalene (pyrido[2,3-d]pyrimidine, 1,8- naphthyridine, 1,8,9-triazaanthracene, 1,5-diazabicyclo [4.3.0]non-5-ene (2,3,4,6,7,8-hexahydro-pyrrolo[1,2-a]pyrimidine), 1,8-diazabicyclo[5.4.0]undec-7-ene (2,3,4,6,7,8,9,10-octahydro-pyrimido[1,2-a]azepine), 2,3-dihydrothieno[3,4-b]-1,4-dioxin, 4H-1,3-oxathiolo[5,4-b]pyrrole, and thieno[3,2-b]furan rings.

Ring A and the additional rings are unsubstituted or substituted with 1 to 4 substituents. Some suitable substituents include lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, carboxyl (hydroxycarbonyl), lower alkanoyl, lower alkanoyloxy, amino, N-(lower alkyl)amino, N,N-di(lower alkyl)amino, formamido (formylamino), N-acylamino, N,N-diacylamino (imido), hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl)hydrazido, carboxamido (carbamoyl), N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl (sulfonic acid), (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl.

In this specification, various substituents are defined as being "lower," which means having 1 to 6 carbon atoms. Lower alkyl groups may be branched or unbranched. Some examples of lower alkyl groups include methyl, ethyl, n-propyl, isopropyl n-butyl, s-butyl, i-butyl, t-butyl, n-pentyl, n-hexyl, 4-methyl-2-pentyl, etc. The lower alkyl group may be unsubstituted or substituted at any position with an aryl, heteroaryl, fluoro, chloro, or bromo group. Lower alkanoyl and lower alkoxy groups contain a lower alkyl portion as defined above, and are unsubstituted or substituted with 1 to 4 groups independently selected from aryl, heteroaryl or fluoro.

Y and Z are substituents at adjacent positions (e.g., 1, 2; ortho) on ring A. Y represents:

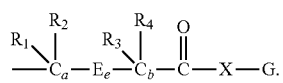

Each of $R^1$ and $R^2$ independently represents H, lower alkyl, aryl, heteroaryl, fluoro, chloro, bromo, lower alkoxy (i.e., alkyloxy), aryloxy, heteroaryloxy, N,N-di(lower alkyl) amino, N,N-diarylamino, N,N-di(heteroaryl)amino, (lower alkyl)thio, arylthio, heteroarylthio, (lower alkane)sulfinyl, arenesulfinyl, heteroarenesulfinyl, (lower alkyl)sulfonyl, arenesulfonyl, heteroarenesulfonyl, (lower alkoxy)-(lower alkyl), aryloxy-(lower alkyl), heteroaryloxy-(lower alkyl), N,N-di(lower alkyl)amino-(lower alkyl), N,N-diarylamino-(lower alkyl), N,N-di(heteroaryl)amino-(lower alkyl), (lower alkyl)thio-(lower alkyl), arylthio-(lower alkyl), heteroarylthio-(lower alkyl), (lower alkane)sulfinyl-(lower alkyl), arenesulfinyl-(lower alkyl), heteroarenesulfinyl-(lower alkyl), (lower alkyl)sulfonyl-(lower alkyl), arenesulfonyl-(lower alkyl), aromatic acyl is benzoyl; (lower alkane)sulfonyl is methanesulfonyl or trifluoromethanesulfonyl; arenesulfonyl is benzenesulfonyl or p-toluenesulfonyl.

In one embodiment, G is hydrogen, a metal ion, a quaternary ammonium ion, or lower alkyl. The metal ion may be any positively charged metal ion. Some examples of suitable metal ions include $Li^+$, $Na^+$, and $K^+$. Some examples of suitable quaternary ammonium ions include $NH_4^+$, $HNEt_3^+$, hydrogen-pyridinium ion, N-methylpyridinium ion, and N-methylmorpholinium ion.

In another embodiment, X-G represents a carbonyl-activating group for the formation of conjugates between the compounds of the invention and a drug. The activating group is any group that makes the carbonyl group sandwiched by $C_b$ and X of the Y component of the invention more prone to react with a nucleophile. Some examples of activating groups X-G include hydroxybenzotriazole-1-oxy, succinimide-N-oxy, p-nitrophenyloxy, and pentafluorophenyloxy radical. Some examples of nucleophiles include alcohols, thiols, and amines.

In the reaction, the nucleophiles displace the carbonyl-activating group X-G. For example, the reaction of a drug or other chemical compound containing an alcohol group with the activated ester results in a new ester bond with said drug or other chemical compound, the reaction of a drug or other chemical compound containing a thiol group with the activated ester results in a thioester bond with said drug or other chemical compound; and the reaction of a drug or other chemical compound containing an amine group with the activated ester results in an amide bond with said drug or other chemical compound.

In another embodiment, G comprises a pharmaceutically active chemical compound (e.g. a drug), or the precursor thereof. Some examples of pharmaceutically active chemical compounds or the precursors thereof, include antitumor drugs, antiangiogenic drugs, multi-drug reversal agents, anti-inflammatory drugs, antibiotics, antibacterial agents, antiparasitic drugs, and analgesics. For the purposes of the invention, the parent pharmaceutically active chemical compound or precursor possesses at least one nucleophilic group capable of reacting with the carboxyl or heteroarenesulfonyl-(lower alkyl), (lower alkoxy)carbonyl, aryloxycarbonyl, heteroaryloxycarbonyl, carboxamido (carbamoyl), N-(lower alkyl)carbamoyl, N,N-(lower alkyl)carbamoyl, N-arylcarbamoyl, N,N-diarylcarbamoyl, N-heteroarylcarbamoyl or N,N-di(heteroaryl)carbamoyl.

Each of $R^3$ and $R^4$ independently represents H, lower alkyl, aryl, heteroaryl, fluoro, lower alkoxy, aryloxy, heteroaryloxy, N,N-di(lower alkyl)amino, N,N-diarylamino, N,N-di(heteroaryl)amino, (lower alkyl)thio, arylthio, heteroarylthio, (lower alkane)sulfinyl, arenesulfinyl, heteroarenesulfinyl, (lower alkyl)sulfonyl, arenesulfonyl, heteroarenesulfonyl, (lower alkoxy)-(lower alkyl), aryloxy-(lower alkyl), heteroaryloxy-(lower alkyl), N,N-di(lower alkyl)amino-(lower alkyl), N,N-diarylamino-(lower alkyl), N,N-di(heteroaryl)amino-(lower alkyl), (lower alkyl)thio-(lower alkyl), arylthio-(lower alkyl), heteroarylthio-(lower alkyl), (lower alkane)sulfinyl-(lower alkyl), arenesulfinyl-(lower alkyl), heteroarenesulfinyl-(lower alkyl), (lower alkyl)sulfonyl-(lower alkyl), arenesulfonyl-(lower alkyl), heteroarenesulfonyl-(lower alkyl), (lower alkoxy)carbonyl, aryloxycarbonyl, heteroaryloxycarbonyl, carboxamido (carbamoyl), N-(lower alkyl)carbamoyl or N,N-(lower alkyl)carbamoyl, N-arylcarbamoyl, N,N-diarylcarbamoyl, N-heteroarylcarbamoyl or N,N-di(heteroaryl)carbamoyl.

$R^1$ and $R^2$ or $R^3$ and $R^4$ are optionally connected to form a 3 to 8 member ring. The ring may be cycloalkyl, heterocycloalkyl, cycloalkenyl, heterocycloalkenyl, aryl, or heteroaryl. Examples of such rings have been previously given.

X and E independently represent O, S, NR$^a$ or NR$^b$. R$^a$ and R$^b$ independently represent H, lower alkyl, cycloalkyl, heterocycloalkyl, cycloalkenyl, heterocycloalkenyl, aryl, aryl lower alkyl, heteroaryl, lower alkanoyl, aromatic acyl (arenecarbonyl), heteroaromatic acyl (heteroarenecarbonyl), (lower alkoxy)carbonyl, aryloxycarbonyl, heteroaryloxycarbonyl, N-arylcarbamoyl, N,N-diarylcarbamoyl, N-heteroarylcarbamoyl, N,N-di(heteroaryl)carbamoyl, (lower alkane)sulfonyl, arenesulfonyl, or heteroarenesulfonyl.

In preferred embodiments, (lower alkoxy)carbonyl is tert-butoxycarbonyl, benzyloxycarbonyl or phenanthrylmethoxycarbonyl; lower alkanoyl is acetyl; thiocarboxyl group or activated ester thereof, of the compounds of the invention, prior to becoming G.

Z represents:

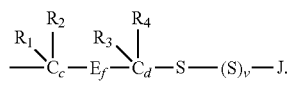

R$^1$, R$^2$, R$^3$, R$^4$, and E in Z are defined as given previously for Y. The subscript v represents 0 or 1, provided that when v is 0, then J is hydrogen, a metal ion, or a quaternary ammonium ion; and X is O and G is H.

In one embodiment, J is a lower alkyl, aryl or heteroaryl group. Some examples of preferred groups include methyl, phenyl, p-fluorophenyl, p-nitrophenyl, o-nitrophenyl, and pyridine-2-yl groups. J groups such as p-nitrophenyl, o-nitrophenyl, or pyridine-2-yl are known to hasten the thiol exchange reaction, and may be regarded as disulfide-activating groups.

In another embodiment, J is a substituent that contains an activated ester, or a precursor thereof, and thus, permits a specific binding agent, such as an antibody, to bind to the disulfide end of the Z component without undergoing a thiol exchange process. Some classes of such J substituents include omega-hydroxycarbonyl-(lower alkyl), omega-(lower alkoxy)carbonyl-(lower alkyl), or omega-(X-G)-carbonyl-(lower alkyl) group, wherein the X-G activating group is defined above. Some suitable examples of such groups include 2-hydroxycarbonylethyl, 2-methoxycarbonylethyl, p-nitrophenyloxycarbonylpropyl, pentafluorophenyloxycarbonylbutyl, 2-(succiminide-N-oxycarbonyl)-1-methylpropyl. As an example, an activated ester substituent J reacts with the lysine residues of a monoclonal antibody, another specific binding protein or a specific binding peptide to form a conjugate.

In another embodiment, J is a specific binding agent. A specific binding agent is a protein, peptide, lectin, saccharide, or other moiety that selectively binds to a molecule on the surface of a cell. Some types of molecules on the surface of a cell that may be targeted by a specific binding agent include receptors, oligosaccharides, lectins, adhesion molecules, proteoglycams, integrins, immunoglobulins, major histocompatibility complex, e.g., human leukocyte antigen, and glycoproteins. Some examples of receptors include tyrosine kinase receptors, such as vascular endothelial growth factor (VEGF) receptor, and epidermal growth factor (EGF) receptors, e.g., HER-1, HER-2, HER-3, and HER-4.

A specific binding agent may, for example, be a receptor-specific ligand. A receptor-specific ligand is a natural or synthetic molecule, such as a hormone or neurotransmitter, which specifically binds to a receptor on the surface of a cell. Some examples of receptor-specific ligands include bombesin, transferrin, VEGF, and EGF.

In another embodiment, the specific binding agent is a molecule that comprises the hypervariable region (CDR) of an antibody and has binding characteristics that are the same as, or comparable to, those of the whole antibody. Preferably, the specific binding agent is an antibody or a functional equivalent of an antibody, such as a fragment of an antibody. More preferably, the antibody is a monoclonal antibody or a functional equivalent derived from a monoclonal antibody.

Suitable fragments of antibodies include any fragment that comprises a sufficient portion of the hypervariable region to bind specifically, and with sufficient affinity, to a molecule on the surface of a cell. Such fragments may, for example, contain one or both Fab fragments, or the F(ab')$_2$ fragment. Preferably, the antibody fragments contain all six complementarity determining regions of the whole antibody, although functional fragments containing fewer than all of such regions, such as three, four or five CDRs, may also be suitable.

The preferred fragments are single chain antibodies, or Fv fragments. Single chain antibodies are polypeptides that comprise at least the variable region of the heavy chain of the antibody linked to the variable region of the light chain, with or without an interconnecting linker. These chains may be produced in bacteria or in eucaryotic cells.

The antibodies and functional equivalents may be members of any class of immunoglobulins, such as: IgG, IgM, IgA, IgD, or IgE, and the subclasses thereof. The preferred antibodies are members of the IgG1 subclass. The functional equivalents may also be equivalents of combinations of any of the above classes and subclasses.

Suitable variable and hypervariable regions of antibodies may be derived from antibodies produced by any mammal in which monoclonal antibodies are made. Some examples of suitable mammals include rabbits, rats, mice, horses, goats, and primates. Preferably, the monoclonal antibodies are derived from mice. The monoclonal antibodies thus obtained are humanized by methods known in the art for the purpose of human clinical use.

In Y and Z, each of a, b, c, d, e and f independently represents 0 or 1, with the provisions that a+c equals 0, 1, or 2; b+d equals 0, 1, or 2; a+b+c+d+e+f equals 1, 2, or 3; additionally provided that when f is 1, then d is 1, and when d is 0, then f is 0; and when both e and b are 0, then neither R$^1$ nor R$^2$ is chloro or bromo.

The compounds of the present invention may be linked to a pharmaceutically active chemical component G, or a precursor thereof, by methods known in the art. For example, the carbonyl group in the compound may first be reacted with a suitable activating compound to attach an activating group X-G. Some examples of activating compounds, or a combination of activating compounds, capable of attaching an activating group X-G onto the compounds of the invention, include the combination of 1,3-diisopropylcarbodiimide (DIC) or 1,3-dicyclohexylcarbodiimide (DCC) with 1-hydroxybenzotriazole; N-hydroxysuccinimide; and p-(N,N-dimethylamino)pyridine (DMAP). The resulting activated ester of the compound is reacted with, for example, a drug or pro-drug bearing a suitable nucleophilic group or groups, as described above. The drug thereby becomes linked to the carboxyl end of the Y component of the compound.

Similarly, the compounds of the present invention may be linked to a specific binding agent by methods known in the art. The disulfide group in component Z will undergo the well known thiol exchange process in the presence of a specific binding agent bearing at least one thiol group. A disulfide-activating group is not required under all conditions, but may be used to hasten the reaction. The specific binding agent thereby becomes linked to the compound through a disulfide group on the Z component.

Alternatively, a specific binding agent may be modified to contain activated disulfide linkages in order to react with the reduced thiol form of the Z component when Y possesses a carboxylic acid terminus, i.e., when v is 0 and J is hydrogen, a metal ion, or a quaternary ammonium ion, and X is O and G is H The disulfide-activated specific binding agent binds to the reduced thiol form of Z through the disulfide exchange process.

The modification of specific binding agents, such as monoclonal antibodies, with an acyl group bearing an activated disulfide moiety is well known in the art. [See R. V. J. Chari, Advanced Drug Delivery Reviews, 1998, 31, 89-104; I. Ojima, X. Geng, X. Wu, C. Qu, C. P. Borella, H. Xie, S. D. Wilhelm, B. A. Leece, L. M. Bartle, V. S. Goldmacher, and R. V. J. Chari, J. Med. Chem. 45, 5620-5623 (2002)]. Specific binding proteins such as monoclonal antibodies bearing thiol groups can be readily generated from activated disulfide derivatives by appropriate reducing agents known in the art. [See, for example, Trail, P. A.; Willner, D.; Knipe, J.; Henderson, A. J.: Lasch, S. J.; Zoeckler, M. E.; TrailSmith, M. D.; Doyle, T. W.; King, H. D.; Casazza, A. M.; Braslawsky, G. R.; Brown, J.; Hofstead, S. J.; Greenfield, R. S.; Firestone, R. A.; Mosure, K.; Kadow, K. F.; Yang, M. B.; Hellstroem, K. E.; Hellstroem, I. "Effect of linker variation on the stability, potency, and efficacy of carcinoma-reactive BR64-doxorubicin immunoconjugates", *Cancer Res.* 1997, 57, 100-105, wherein dithiothreitol (DTT) was used as reducing agent.]

The resulting conjugate containing the specific binding agent may be further coupled to, for example, a drug, bearing a hydroxyl, thiol, or amine moiety through the condensation reaction between the carboxylic acid terminus in the Y component of the conjugate via an activated ester, as described above.

In a preferred embodiment, G is a pharmaceutically active chemical compound, preferably a drug, and J is a specific binding agent, preferably a molecule comprising the hypervariable region (CDR) of an antibody. The above combination of G and J forms a linker drug conjugate.

Although not bound by any theory, the invention is believed to work as follows. First, the linker drug conjugate binds to a cell by the attachment of the specific binding agent. The linker drug conjugate is internalized into the cell through, for example, endocytosis. Once inside the cell, the disulfide bond of the linker drug conjugate undergoes cleavage by an endogenous peptide that cleaves disulfide bonds, e.g., glutathione (GT). Glutathione is found in most mammalian cells and its level is considerably elevated in hypoxic cells such as tumor cells. The cleavage of the disulfide bond causes the release of the specific binding agent. Simultaneously, a thiolactonization process occurs between the remaining sulfur atom and the ester, thioester or amide linkage of the drug. The end result of the thiolactonization process is the release of the original and the most active form of the drug, inside of the targeted cell. The reaction scheme below is provided for further elucidation of the process.

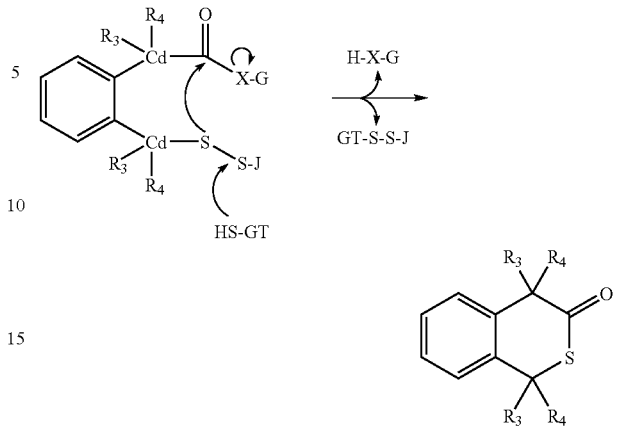

The linker drug conjugate is either uncharged or in the form of pharmaceutically acceptable salts. The term "pharmaceutically acceptable salt" refers to a salt prepared from a suitable linker drug conjugate and, for example, an acid or a base. The salt is acceptably non-toxic and has acceptable pharmacokinetics.

Such salts are formed by well known procedures. Suitable acids for producing salts of the linker drug conjugates include mineral acids and organic acids. Some examples of mineral acids include hydrochloric, hydriodic, hydrobromic, phosphoric, metaphosphoric, nitric and sulfuric acids. Some examples of organic acids include tartaric, acetic, citric, malic, benzoic, pyridine, gluconic, gulonic, succinic, arenesulfonic, e.g. p-toluenesulfonic acids, and the like.

Suitable bases for producing salts of the linker drug conjugates include inorganic bases and organic bases. Some examples of inorganic bases include hydroxides of lithium, sodium, potassium, magnesium and calcium. Some examples of organic bases include primary, secondary, and tertiary, alkyl amines For the pharmaceutical purposes described above, the linker drug conjugate of the invention can be formulated in pharmaceutical preparations optionally including a suitable pharmaceutical carrier (vehicle) or excipient. In this specification, a pharmaceutical carrier is considered synonymous with a vehicle or an excipient as understood by practitioners in the art. Examples of carriers include starch, milk, sugar, certain types of clay, gelatin, stearic acid or salts thereof, magnesium or calcium stearate, talc, vegetable fats or oils, gums and glycols.

The linker drug conjugate formulation may also comprise one or more of the following: a stabilizer, a surfactant, a salt, a buffering agent, or a combination thereof. The stabilizer may be, for example, an amino acid, such as glycine; or an oligosaccharide, such as sucrose, tetralose, lactose or a dextran. Alternatively, the stabilizer may be a sugar alcohol, such as mannitol; or a combination thereof.

Some examples of suitable surfactants include Tween 20, Tween 80; a polyethylene glycol or a polyoxyethylene polyoxypropylene glycol, such as Pluronic F-68 at from about 0.001% (w/v) to about 10% (w/v). The salt or buffering agent may be any salt or buffering agent, such as, for example, sodium chloride, or sodium/potassium phosphate, respectively.

The linker drug conjugate formulation may additionally contain one or more conventional additives. Some examples of such additives include a solubilizer such as, for example, glycerol; an antioxidant such as, for example, benzalkonium chloride (a mixture of quaternary ammonium compounds, known as "quart"), benzyl alcohol, chloretone or chlorobutanol; an anaesthetic agent such as, for example, a morphine derivative; an isotonic agent, or a combination of these. As a precaution against oxidation or other spoilage, the linker drug conjugate formulation may be stored under nitrogen gas in vials sealed with impermeable stoppers.

For aqueous suspensions, emulsifying agents, suspending agents, or a combination thereof, may be added. In addition, coloring, sweetening, and flavoring agents may be added to the formulation. Sterile solutions of the linker drug conjugates can also be employed. If required, the pH of the solutions can be suitably adjusted and buffered.

The linker drug conjugates may be administered alone or as an adjunct with other conventional drugs for treating conditions or diseases, including cancer. The linker drug conjugates may be administered by any method known in the art. Some examples of suitable modes of administration include oral, systemic, and topical administration.

Liquid or solid oral formulations are known in the art. Some examples of formulations suitable for oral administration include tablets, capsules, pills, troches, elixirs, suspensions, and syrups.

Systemic administration includes enteral or parenteral modes of administration, e.g., intravenous; intramuscular; subcutaneous; or intraperitoneal. For example, the linker drug conjugate formulation may be administered by injection of a solution or suspension; or intranasally, in the form of, for example, a nebulizer, liquid mist, or intranasal spray; or transdermally, in the form of, for example, a patch; or rectally, in the form of, for example, a suppository; or intrabronchially, in the form of, for example, an inhaler spray.

The timing of the administration of the linker drug conjugate formulation may also be modified. For example, the formulation may be administered intermittently or by controlled release. Controlled release administration is a method of drug delivery to achieve a certain level of the drug over a particular period of time.

Examples have been set forth below for the purpose of illustration and to describe the best mode of the invention at the present time. However, the scope of this invention is not to be in any way limited by the examples set forth herein.

Example 1

Preparation of (2-mercaptophenyl)acetic acid

2-Oxo-2,3-dihydrobenzo[b]thiophene was prepared by the literature method (Lumma, W. C., Jr.; Dutra, G. A.; Voeker, C. A. *J. Org. Chem.* 1970, 35, 3442-3444; Bordwell, F. G.; Fried, H. E. *J. Org. Chem.* 1991, 56, 4218-4223) from commercially available benzo[b]thiophene (Aldrich Chemicals Co.) in high yield. 2-oxo-2,3-dihydrobenzo[b]thiophene (457 mg, 3.04 mmol), thus obtained, was added to a solution of KOH (1 N, 15 mL) and THF (5 mL). The solution was stirred at 60° C. for 14 h, cooled to ambient temperature, and acidified to pH 2 with 5 N hydrochloric acid. The reaction mixture was extracted with $CH_2Cl_2$ three times. The organic layers were combined, dried over anhydrous $MgSO_4$, filtered, and concentrated in vacuo, affording 449 mg (88% yield) of the (2-mercaptophenyl)acetic acid product in the form of a pale yellow waxy solid: $^1H$ NMR (400 MHz, $CDCl_3$) δ (ppm): 3.53 (s, 1H), 3.85 (s, 2H), 7.22 (m, 3H), 7.45 (m, 1H), 11.82 (broad s, 1H).

Example 2

Preparation of (5-fluoro-2-mercaptophenyl)acetic acid

By the same method as described in Example 1, (5-fluoro-2-mercaptophenyl)acetic acid was prepared from 5-fluoro-3H-benzo[b]thiophen-2-one in 95% yield in the form of a pale yellow solid: $^1H$ NMR (400 MHz, $CDCl_3$) δ (ppm): 3.40 (s, 1H), 3.84 (s, 2H), 6.92 (ddd, J=8.4 Hz, 8.4 Hz, 2.8 Hz, 1H), 7.00 (dd, J=9.2 Hz, 2.8 Hz 1H), 7.42 (dd, J=8.4 Hz, 5.6 Hz, 1H), 11.41 (s, broad, 1H); $^{19}F$ NMR (282 MHz, $CDCl_3$) δ (ppm): −113.05

Example 3

3-(2-Mercaptophenyl)-3-methylbutanoic acid

By the same method as described in Example 1,3-(2-mercaptophenyl)-3-methylbutanoic acid was prepared from 4,4-dimethyl-2-oxo-3,4-dihydro-2H-1-benzothiopyran in 85% yield in the form of a pale yellow solid: $^1H$ NMR ($CDCl_3$, 300 MHz) δ (ppm): 1.58 (s, 6H), 3.12 (s, 2H), 3.66 (s, 1H), 7.2-7.4 (m 4H), 10.2 (broad, 1H).

Example 4

Preparation of (2-methyldisulfanylphenyl)acetic acid

To a solution of (2-mercaptophenyl)acetic acid (449 mg) in $H_2O$ (15 mL) and ethanol (7 mL) was added methyl methanethiosulfonate (372 mg, 2.93 mmol). After stirring for 20 hours, the reaction mixture was diluted with ether and washed with 1 N KOH twice. The water layers were combined and acidified to pH 2 with 5 N hydrochloric acid. This solution was extracted with $CH_2Cl_2$ three times. The organic layers were combined, dried over anhydrous $MgSO_4$, filtered, and concentrated in vacuo to afford 576 mg (100% yield) of the (2-methyl disulfanylphenyl)acetic acid product in the form of a yellow oil: $^1H$ NMR (400 MHz, $CDCl_3$) δ (ppm): 2.42 (s, 3H), 3.92 (s, 2H), 7.10-7.40 (m, 3H), 7.80 (d, J=7.6 Hz, 1H), 10.34 (s, 1H); $^{13}C$ NMR (100 MHz, $CDCl_3$) δ (ppm): 22.7, 38.9, 127.8, 128.1, 128.3, 128.8, 130.4, 130.8, 130.9, 177.1. HRMS (EI): m/e calcd. for $C_9H_{10}O_2S_2$: 214.012223, Found: 214.012637 (Δ=−1.9 ppm).

Example 5

(5-Fluoro-2-methyldisulfanylphenyl)acetic acid

By the same method as described in Example 4, (5-fluoro-2-methyldisulfanylphenyl) acetic acid was prepared from (5-fluoro-2-mercaptophenyl)acetic acid in 74% yield in the form of a light yellow solid: $^1H$ NMR (400 MHz, $CDCl_3$) δ (ppm): 2.43 (s, 3H), 3.94 (s, 2H), 7.05 (m, 2H), 7.74 (m, 1H), 10.93 (s, broad, 1H); $^{19}F$ NMR (282 MHz, $CDCl_3$) δ (ppm): −113.06

Example 6

3-Methyl-3-(2-methyldisulfanylphenyl)butanoic acid

By the same method as described in Example 4, 3-methyl-3-(2-methyldisulfanylphenyl) butanoic acid was prepared from 3-(2-mercaptophenyl)-3-methylbutanoic acid in 75% yield in the form of an oil: $^1$H NMR (CDCl$_3$, 300 MHz) δ (ppm): 1.58 (s, 6H), 2.43 (s, 3H), 3.14 (s, 2H), 7.1-7.4 (m, 3H), 7.94 (d, J=7.8 Hz, 1H), 10.4 (broad, 1H), $^{13}$C-NMR (CDCl$_3$, 75 MHz) δ (ppm): 22.6, 29.4, 38.4, 44.5, 126.9, 127.2, 127.4, 130.5, 135.4, 145.7, 176.6.

Example 7

3-Methyl-3-[2-(pyridine-2-yldisulfanyl)phenyl]butanoic acid

To a solution of 3-(2-mercaptophenyl)-3-methylbutanoic acid (227 mg) in aqueous THF was added 2,2'-dipyridyl disulfide (363 mg), and the mixture was stirred for 15 hours at 40° C. The reaction was quenched by 1 N hydrochloric acid. The reaction mixture was extracted by ethyl acetate at pH 1, and the extract was dried over anhydrous MgSO$_4$ and concentrated in vacuo. The crude product was purified on a silica gel column to afford 252 mg (75% yield) of the 3-methyl-3-[2-(pyridine-2-yldisulfanyl)phenyl]butanoic acid product in the form of a light yellow solid: mp 122-125° C., $^1$H NMR (CDCl$_3$, 300 MHz) δ (ppm): 1.67 (s, 6H), 3.32 (s, 2H), 7.11 (m, 1H), 7.17 (m, 2H), 7.38 (m, 1H), 7.5-7.6 (m, 2H), 7.80 (m, 1H), 8.44 (d, J=4.5 Hz, 1H), 10.52 (broad s, 1H).

Example 8

4-Fluorophenyl 3-methyl-3-(2-methyldisulfanylphenyl)butanoate

To a mixture of 3-methyl-3-(2-methyldisulfanylphenyl) butanoic acid, 4-fluorophenol (1.1 eq) and 4-(N,N-dimethylamino)pyridine (0.5 eq) in CH$_2$Cl$_2$ was added diisopropylcarbodiimide (1.5-2.0 eq) at 0° C. The mixture was stirred overnight at ambient temperature. The precipitate was filtered off and the filtrate concentrated by rotary evaporation. The crude product was purified on a silica gel column to afford 4-fluorophenyl 3-methyl-3-(2-methyldisulfanylphenyl) butanoate as a colorless oil in 62% yield: $^1$H NMR (CDCl$_3$, 300 MHz) δ (ppm): 1.76 (s, 6H), 2.52 (s, 3H), 3.44 (s, 2H), 6.70 (dd, J=9.0, 4.2 Hz, 2H), 7.00 (t, J=9.0 Hz, 2H), 7.2-7.3 (m, 2H), 7.36 (dd, J=7.8, 1.5 Hz, 1H), 7.96 (dd, J=7.8, 1.2 Hz, 1H). $^{19}$F NMR (CD$_3$CN, 282 MHz) δ (ppm): −119.2.

Example 9

4-Fluorophenyl 3-methyl-3-[2-(pyridine-2-yldisulfanyl)phenyl]butanoate

By the same method as described in Example 8, 4-fluorophenyl 3-methyl-3-[2-(pyridine2-yldisulfanyl)phenyl]butanoate was prepared in the form of a colorless viscous oil in 66% yield: $^1$H NMR (CDCl$_3$, 300 MHz) δ (ppm): 1.74 (s, 6H), 3.43 (s, 2H), 6.60 (m, 2H), 6.93 (m, 2H), 7.07 (m, 1H), 7.20 (m, 2H), 7.42 (m, 2H), 7.59 (d, J=7.8 Hz, 1H), 7.77 (m, 1H), 8.46 (d, J=3.6 Hz, 1H). $^{19}$F NMR (CD$_3$CN, 282 MHz) δ (ppm): −119.1.

Example 10

Preparation of 2'-(methyldisulfanylphenyl)acetyl-3'-dephenyl-3'-(2-methylpropyl)-10-propanoyldocetaxel To a solution of 3'-dephenyl-3'-(2-methylpropyl)-10-propanoyldocetaxel (12.6 mg, 0.015 mmol) and (2-methyldisulfanylphenyl)acetic acid (6.7 mg, 0.031 mmol) in CH$_2$Cl$_2$ (2 mL) was added diisopropylcarbodiimide (3.8 mg, 0.03 mmol) and 4-(N,N-dimethylamino)pyridine (1.8 mg, 0.015 mmol). The reaction mixture was stirred for 2.5 hours, and then concentrated in vacuo. Purification of the crude product by column chromatography on silica gel using hexans/EtOAc (3/1 to 2/1) as eluent afforded 13.2 mg (85% yield) of the 2'-(2-methyldisulfanylphenyl)acetyl-3'-dephenyl-3'-(2-methylpropyl)-10-propanoyldocetaxel product in the form of a white solid; $^1$H NMR (400 MHz, CDCl$_3$) δ (ppm): 0.92 (m, 6H), 1.13 (s, 3H), 1.22-1.27 (m, 6H), 1.30 (s, 9H), 1.67 (s, 3H), 1.87 (m, 3H), 1.88 (s, 3H), 2.36 (s, 3H), 2.40 (s, 2H), 2.44 (s, 3H), 2.46 (m, 1H), 2.54 (m, 2H), 3.80 (d, J=7.2 Hz, 1H), 3.92 (d, J=16.4 Hz, 1H), 4.06 (d, J=16.4 Hz, 1H), 4.18 (d, J=8.4 Hz, 1H), 4.29 (m, 2H), 4.42 (dd, J=10.2, 6.7 Hz, 1H), 4.58 (d, J=10.4 Hz, 1H), 4.90 (d, J=2.8 Hz, 1H) (H$_2$), 4.97 (d, J=8.0 Hz, 1H), 5.65 (d, J=7.0 Hz, 1H), 6.19 (m, 1H), 6.29 (s, 1H), 7.30 (m, 3H), 7.47 (t, J=7.6 Hz, 2H), 7.59 (t, J=7.6 Hz, 1H), 7.77 (d, J=7.6 Hz, 1H), 8.11 (d, J=7.2 Hz, 2H); $^{13}$C NMR (100 MHz, CDCl$_3$) δ (ppm): 9.0, 9.5, 14.8, 21.9, 22.5, 22.7, 23.0, 24.6, 26.5, 27.5, 28.1, 29.7, 35.4, 38.8, 41.1, 43.1, 45.6, 48.9, 58.4, 71.7, 72.1, 74.6, 75.1, 75.4, 76.4, 79.3, 79.8, 80.9, 84.4, 128.0, 128.4, 128.6, 129.2, 130.2, 130.3, 131.0, 132.3, 133.5, 143.4, 155.3, 163.4, 167.0, 168.2, 169.6, 170.1, 174.6, 204.0. HRMS (FAB): m/e calcd. for C$_{53}$H$_{69}$NO$_{16}$S$_2$H$^+$: 1040.413605. Found: 1040.413600 (Δ=0.0 ppm).

Example 11

Preparation of 2'-(5-fluoro-2-methyldisulfanylphenyl)acetyl-3'-dephenyl-3'-(2-methylpropyl)-10-propanoyldocetaxel By the same method as described in Example 10, 2'-(5-fluoro-2-methyldisulfanylphenyl) acetyl-3'-dephenyl-3'-(2-methylpropyl)-10-propanoyldocetaxel was prepared from 3'-dephenyl-3'-(2-methylpropyl)-10-propanoyldocetaxel and (5-fluoro-2-methyldisulfanyl phenyl)acetic acid in 75% yield in the form of a white solid: $^1$H NMR (400 MHz, CDCl$_3$) δ (ppm): 0.94 (m, 6H), 1.13 (s, 3H), 1.20-1.25 (m, 6H), 1.30 (s, 9H), 1.60 (s, 3H), 1.65 (s, 2H), 1.66 (s, 3H), 1.90 (s, 3H), 2.36 (s, 3H), 2.43 (s, 3H), 2.48 (m, 1H), 2.54 (m, 2H), 3.80 (d, J=7.2 Hz, 1H), 3.95 (d, J=16.4 Hz, 1H), 4.08 (d, J=16.4 Hz, 1H), 4.19 (d, J=8.4 Hz, 1H), 4.29 (d, J=8.4 Hz, 1H), 4.33 (m, 1H), 4.44 (dd, J=10.2, 6.7 Hz, 1H), 4.57 (d, J=10.4 Hz, 1H), 4.91 (d, J=2.0 Hz, 1H), 4.97 (d, J=8.0 Hz, 1H), 5.66 (d, J=7.2 Hz, 1H), 6.19 (t, J=8.0 Hz, 1H), 6.29 (s, 1H), 7.04 (m, 1H), 7.10 (dd, J=9.2, 2.8 Hz, 1H), 7.47 (t, J=7.2 Hz, 2H), 7.59 (t, J=7.2 Hz, 1H), 7.71 (dd, J=8.4, 5.6 Hz, 1H), 8.11 (d, J=7.2 Hz, 2H); $^{19}$F NMR (282 MHz, CDCl$_3$) δ (ppm): −112.84.

Example 12

Cleavage of the Disulfide Bond in the Drug-Linker Conjugate

In order to confirm that the designed drug-release mechanism works under physiological conditions, a control experiment was performed using an anticancer linker drug conjugate and cysteine as a model of glutathione. The results of the experiment below provide clear evidence that the drug is released according to the desired mechanism of the invention.

To a solution of the drug-linker conjugate, 2'-(5-fluoro-2-methyldisulfanylphenyl) acetyl-3'-dephenyl-3'-(2-methylpropyl)-10-propanoyldocetaxel, (4.8 mg, 0.0045 mmol) in CH$_3$CN (1.1 mL) was added cysteine (2.20 mg, 0.018 mmol) in buffer (pH 7.0, 0.56 mL) solution. The mixture was stirred at room temperature. The progress of the disulfide cleavage and drug release process was monitored by HPLC [Conditions: C-18 column. Flow rate: H$_2$O, 0.6 mL/min; CH$_3$CN, 0.4 mL/min., ambient temperature] periodically. The formations of thiolactone (5-fluoro-3H-benzo[b]thiophen-2-one) (retention time=9.05 min) and taxoid (3'-dephenyl-3'-(2-methylpropyl)-10-propanoyldocetaxel) (retention time=14.01 min) as well as the disappearance of the drug-linker conjugate (retention time=18.20 min) was clearly observed. After 2 hours, the drug-linker conjugate completely disappeared and the clean release of the taxoid together with the formation of the thiolactone was confirmed.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

I claim:

1. A compound having the formula Y-A-Z, wherein:
    A is a phenyl group;
    ring A is unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, hydroxycarbonyl, lower alkanoyl, lower alkanoyloxy, amino, N-(lower alkyl)amino, N,N-di(lower alkyl)amino, formylamino, N-acylamino, N,N-diacylamino, hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl) hydrazido, carbamoyl, N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl, (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroarylox-ysulfonyl-(lower alkyl), (lower alkane)sulfonyl, arenesulfonyl, or heteroarenesulfonyl;
    Y and Z are substituents at adjacent positions on ring A;
    Y represents:

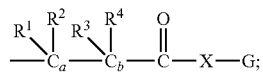

Z represents:

X represents O or S;
    R$^1$, R$^2$, R$^3$ and R$^4$ independently represent H, lower alkyl or lower alkoxy, wherein the lower alkyl and lower alkoxy groups are unsubstituted or substituted with groups independently selected from aryl, heteroaryl or fluoro, wherein R$^1$ and R$^2$ or R$^3$ and R$^4$ are optionally connected to form a 3 to 8 member ring, wherein the 3 to 8 member ring is cycloalkyl, heterocycloalkyl, cycloalkenyl, heterocycloalkenyl, aryl, or heteroaryl;
    each of a and b independently represents 0 or 1;
    a+b equals 1 or 2;
    G is a metal ion, a quaternary ammonium ion, or comprised of a pharmaceutically active chemical compound or the precursor thereof, wherein said pharmaceutically active chemical compound or precursor thereof possesses at least one nucleophilic group prior to becoming G; or X-G represents a carbonyl-activating group selected from the group consisting of hydroxybenzotriazole-1-oxy, succinimide-N-oxy, p-nitrophenyloxy and pentafluorophenyloxy radical;
    J is lower alkyl, aryl, heteroaryl, omega-hydroxycarbonyl-(lower alkyl), omega-(lower alkoxy)carbonyl-(lower alkyl), or comprised of a specific binding agent, wherein a specific binding agent is a protein, peptide, lectin, saccharide, or other moiety that selectively binds to a molecule on the surface of a cell; or omega-(X-G)-carbonyl-(lower alkyl) group, wherein X-G is a carbonyl-activating group defined above.

2. A compound according to claim 1 wherein X represents O.

3. A compound according to claim 1 wherein X represents S.

4. A compound according to claim 1 wherein R$^1$ and R$^2$ are independently H or methyl.

5. A compound according to claim 1 wherein R$^3$ and R$^4$ are independently H or methyl.

6. A compound according to claim 1 wherein a and b represent 1.

7. A compound according to claim 1 wherein a represents 1; b represents 0.

8. A compound according to claim 1 wherein b represents 1; a represents 0.

9. A compound according to claim 1 wherein G comprises a pharmaceutically active chemical compound.

10. A compound according to claim 9 wherein the pharmaceutically active chemical compound is a taxoid.

11. A compound according to claim 1 wherein J represents a specific binding agent.

12. A compound according to claim 11 wherein the specific binding agent comprises a hypervariable region of a monoclonal antibody.

13. A compound having the formula Y-A-Z, wherein A is a phenyl group;
    ring A is unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, hydroxycarbonyl, lower alkanoyl, lower alkanoyloxy, amino, N-(lower alkyl)amino, N,N-di(lower alkyl)amino, formylamino, N-acylamino, N,N-diacylamino, hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl) hydrazido, carbamoyl, N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl, (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl;

Y and Z are substituents at adjacent positions on ring A;

Y represents:

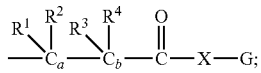

Z represents:

a is 1; $R^1$ and $R^2$ are methyl; b is 1; $R^3$ and $R^4$ are hydrogen; X represents O; G is a taxoid; and J is an omega-(succinimide-N-oxycarbonyl)-1-(lower alkyl) wherein the lower alkyl is methylpropyl.

14. A compound having the formula Y-A-Z, wherein:

A is a phenyl group;

ring A is unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, hydroxycarbonyl, lower alkanoyl, lower alkanoyloxy, amino, N-(lower alkyl)amino, N,N-di(lower alkyl)amino, formylamino, N-acylamino, N,N-diacylamino, hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl)hydrazido, carbamoyl, N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl, (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl;

Y and Z are substituents at adjacent positions on ring A;

Y represents:

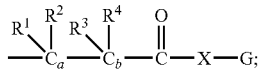

Z represents:

X represents O or S;

$R^1$, $R^2$, $R^3$ and $R^4$ independently represent H, lower alkyl or lower alkoxy, wherein the lower alkyl and lower alkoxy groups are unsubstituted or substituted with groups independently selected from aryl, heteroaryl or fluoro, wherein $R^1$ and $R^2$ or $R^3$ and $R^4$ are optionally connected to form a 3 to 8 member ring, wherein the 3 to 8 member ring is cycloalkyl, heterocycloalkyl, cycloalkenyl, heterocycloalkenyl, aryl, or heteroaryl;

each of a and b independently represents 0 or 1; a+b equals 1 or 2;

G is hydrogen, a metal ion, a quaternary ammonium ion, lower alkyl, or comprised of a pharmaceutically active chemical compound or the precursor thereof, wherein said pharmaceutically active chemical compound or precursor thereof possesses at least one nucleophilic group prior to becoming G; or X-G represents a carbonyl-activating group selected from the group consisting of hydroxybenzotriazole-1-oxy, succinimide-N-oxy, p-nitrophenyloxy and pentafluorophenyloxy radical;

J is lower alkyl, heteroaryl, omega-hydroxycarbonyl-(lower alkyl), omega-(lower alkoxy)carbonyl-(lower alkyl), or comprised of a specific binding agent, wherein a specific binding agent is a protein, peptide, lectin, saccharide, or other moiety that selectively binds to a molecule on the surface of a cell; or omega-(X-G)-carbonyl-(lower alkyl) group, wherein X-G is a carbonyl-activating group defined above.

15. A compound according to claim 14 wherein X represents O.

16. A compound according to claim 14 wherein X represents S.

17. A compound according to claim 14 wherein a and b represent 1.

18. A compound according to claim 14 wherein a represents 1; b represents 0.

19. A compound according to claim 14 wherein b represents 1; a represents 0.

20. A compound according to claim 14 wherein G comprises a pharmaceutically active chemical compound.

21. A compound having the formula Y-A-Z, wherein:

A is a phenyl group;

ring A is unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, hydroxycarbonyl, lower alkanoyl, lower alkanoyloxy, amino, N-(lower alkyl)amino, N,N-di(lower alkyl)amino, formylamino, N-acylamino, N,N-diacylamino, hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl)hydrazido, carbamoyl, N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl, (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl;

Y and Z are substituents at adjacent positions on ring A;

Y represents:

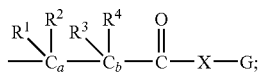

Z represents:

X represents S;

$R^1, R^2, R^3$ and $R^4$ independently represent H, lower alkyl or lower alkoxy, wherein the lower alkyl and lower alkoxy groups are unsubstituted or substituted with groups independently selected from aryl, heteroaryl or fluoro, wherein $R^1$ and $R^2$ or $R^3$ and $R^4$ are optionally connected to form a 3 to 8 member ring, wherein the 3 to 8 member ring is cycloalkyl, heterocycloalkyl, cycloalkenyl, heterocycloalkenyl, aryl, or heteroaryl;

each of a and b independently represents 0 or 1;

a+b equals 1 or 2;

G is a metal ion, a quaternary ammonium ion, lower alkyl, or comprised of a pharmaceutically active chemical compound or the precursor thereof, wherein said pharmaceutically active chemical compound or precursor thereof possesses at least one nucleophilic group prior to becoming G; or X-G represents a carbonyl-activating group selected from the group consisting of hydroxybenzotriazole-1-oxy, succinimide-N-oxy, p-nitrophenyloxy and pentafluorophenyloxy radical;

J is lower alkyl, aryl, heteroaryl, omega-hydroxycarbonyl-(lower alkyl), omega-(lower alkoxy)carbonyl-(lower alkyl), or comprised of a specific binding agent, wherein a specific binding agent is a protein, peptide, lectin, saccharide, or other moiety that selectively binds to a molecule on the surface of a cell; or omega-(X-G)-carbonyl-(lower alkyl) group, wherein X-G is a carbonyl-activating group defined above.

22. A compound having the formula Y-A-Z, wherein:

A is a phenyl group;

ring A is unsubstituted or substituted with 1 to 4 substituents selected from lower alkyl, aryl, heteroaryl, hydroxy-(lower alkyl), amino-(lower alkyl), N-(lower alkyl)amino-(lower alkyl), N,N-di(lower alkyl)amino-(lower alkyl), N-arylamino-(lower alkyl), N,N-diarylamino-(lower alkyl), N-(heteroaryl)amino-(lower alkyl), N,N-di(heteroaryl)amino-(lower alkyl), hydroxylamino, O-(lower alkoxy)amino, O-aryloxyamino, O-heteroaryloxyamino, fluoro, chloro, bromo, nitro, hydroxyl, lower alkoxy, aryloxy, hydroxycarbonyl, lower alkanoyl, lower alkanoyloxy, amino, N-(lower alkyl)amino, N,N-di(lower alkyl)amino, formylamino, N-acylamino, N,N-diacylamino, hydrazido, N-(lower alkyl)hydrazido, N,N-di(lower alkyl)hydrazido, N-arylhydrazido, N,N-diarylhydrazido, N-(heteroaryl)hydrozido, N,N-di(heteroaryl) hydrazido, carbamoyl, N-(lower alkyl)carbamoyl, N,N-(lower alkyl)carbamoyl, N-arylcarbamoyl, N,N-diarylcarbamoyl, N-heteroarylcarbamoyl, N,N-di(heteroaryl)carbamoyl, hydroxysulfonyl, (lower alkoxy)sulfonyl, aryoxysulfonyl, heroaryloxysulfonyl, hydroxysulfonyl-(lower alkyl), (lower alkoxy)sulfonyl-(lower alkyl), aryoxysulfonyl-(lower alkyl), heroaryloxysulfonyl-(lower alkyl), (lower alkane)sulfonyl, arenesulfonyl, or heteroarenesulfonyl;

Y and Z are substituents at adjacent positions on ring A;

Y represents:

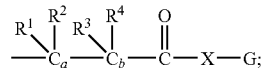

Z represents:

X represents O or S;

$R^1, R^2, R^3$ and $R^4$ independently represent H, lower alkyl or lower alkoxy, wherein the lower alkyl and lower alkoxy groups are unsubstituted or substituted with groups independently selected from aryl, heteroaryl or fluoro, wherein $R^1$ and $R^2$ or $R^3$ and $R^4$ are optionally connected to form a 3 to 8 member ring, wherein the 3 to 8 member ring is cycloalkyl, heterocycloalkyl, cycloalkenyl, heterocycloalkenyl, aryl, or heteroaryl;

each of a and b independently represents 0 or 1;

a+b equals 1 or 2;

G is a metal ion, a quaternary ammonium ion, lower alkyl, or comprised of a pharmaceutically active chemical compound or the precursor thereof, wherein said pharmaceutically active chemical compound or precursor thereof possesses at least one nucleophilic group prior to becoming G; or X-G represents a carbonyl-activating group selected from the group consisting of hydroxybenzotriazole-1-oxy, succinimide-N-oxy, p-nitrophenyloxy and pentafluorophenyloxy radical;

J is comprised of a specific binding agent, wherein a specific binding agent is a protein, peptide, lectin, saccharide, or other moiety that selectively binds to a molecule on the surface of a cell.

23. A compound according to claim 22 wherein the specific binding agent comprises a hypervariable region of a monoclonal antibody.

* * * * *

UNITED STATES PATENT AND TRADEMARK OFFICE
CERTIFICATE OF CORRECTION

PATENT NO. : 7,847,119 B2
APPLICATION NO. : 11/856317
DATED : December 7, 2010
INVENTOR(S) : Iwao Ojima Page 1 of 1

It is certified that error appears in the above-identified patent and that said Letters Patent is hereby corrected as shown below:

Column 1, line 36:

Now reads: "(usually the parent drug itself."

Should read: --(usually the parent drug itself).--

Column 8, lines 56-57:

Now reads: "dibenzo[b]azepine, 5H-dibenzo[b]azepine-5-carboxamide,"

Should read: --dibenzo[b,f]azepine, 5H-dibenzo[b,f]azepine-5-carboxamide,--

Signed and Sealed this
Fourth Day of September, 2012

David J. Kappos
*Director of the United States Patent and Trademark Office*

UNITED STATES PATENT AND TRADEMARK OFFICE
CERTIFICATE OF CORRECTION

PATENT NO. : 7,847,119 B2
APPLICATION NO. : 11/856317
DATED : December 7, 2010
INVENTOR(S) : Iwao Ojima It is certified that error appears in the above-identified patent and that said Letters Patent is hereby corrected as shown below:

Column 1, lines 12-15:

Now reads: "The present invention was made with government support under Grant No. R01 GM427980 as well as R01CA103314 awarded by the National Institutes of Health. The United States government has certain rights in this invention."

Should read: -- This invention was made with government support under grant numbers GM427980 and CA103314 awarded by the National Institutes of Health. The government has certain rights in the invention. --

Signed and Sealed this
Twenty-third Day of October, 2012

David J. Kappos
*Director of the United States Patent and Trademark Office*